(12) United States Patent
Mark et al.

(10) Patent No.: US 11,492,189 B2
(45) Date of Patent: Nov. 8, 2022

(54) CONTACT LENS PACKAGING SOLUTIONS CONTAINING HYDROPHILIC POLYMERS ENDCAPPED WITH A HYDROPHILIC AND A HYDROPHOBIC GROUP

(71) Applicant: Bausch & Lomb Incorporated, Rochester, NY (US)

(72) Inventors: Analuz Mark, Spencerport, NY (US); Ivan M. Nuñez, Penfield, NY (US); Vicki L. Barniak, Fairport, NY (US); Jennifer M. Hunt, Lake Grove, NY (US); Lynn Coullard, Williamson, NY (US); Keyla M. Cubi, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 250 days.

(21) Appl. No.: 16/774,190

(22) Filed: Jan. 28, 2020

(65) Prior Publication Data

US 2020/0239217 A1    Jul. 30, 2020

Related U.S. Application Data

(60) Provisional application No. 62/798,096, filed on Jan. 29, 2019.

(51) Int. Cl.
| | | |
|---|---|---|
| *C11D 9/36* | (2006.01) | |
| *B65D 81/22* | (2006.01) | |
| *A45C 11/00* | (2006.01) | |
| *C07D 263/34* | (2006.01) | |
| *C08F 283/12* | (2006.01) | |
| *C08F 290/06* | (2006.01) | |
| *C11D 3/00* | (2006.01) | |
| *C11D 3/48* | (2006.01) | |

(52) U.S. Cl.
CPC ............ *B65D 81/22* (2013.01); *A45C 11/005* (2013.01); *C07D 263/34* (2013.01); *C08F 283/124* (2013.01); *C08F 290/068* (2013.01); *B65D 2585/545* (2013.01); *C11D 3/0047* (2013.01); *C11D 3/0078* (2013.01); *C11D 3/48* (2013.01)

(58) Field of Classification Search
CPC .......... C11D 3/0078; G02B 1/04; B65B 55/14
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,143,949 A | 3/1979 | Chen |
| 4,153,641 A | 5/1979 | Deichert et al. |
| 4,195,030 A | 3/1980 | Deichert et al. |
| 4,197,266 A | 4/1980 | Clark et al. |
| 4,208,506 A | 6/1980 | Deichert et al. |
| 4,312,575 A | 1/1982 | Peyman et al. |
| 4,327,203 A | 4/1982 | Deichert et al. |
| 4,355,147 A | 10/1982 | Deichert et al. |
| 4,555,732 A | 11/1985 | Tuhro |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Nandu et al. |
| 5,271,876 A | 12/1993 | Ibar |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,464,667 A | 11/1995 | Kohler et al. |
| 5,512,205 A | 4/1996 | Lai |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler et al. |
| 5,908,906 A | 6/1999 | Kunzler et al. |
| 6,699,435 B2 | 3/2004 | Salpekar |
| 7,915,323 B2 | 3/2011 | Awasthi et al. |
| 7,919,136 B2 | 4/2011 | Linhardt et al. |
| 7,994,356 B2 | 8/2011 | Awasthi et al. |
| 8,420,711 B2 | 4/2013 | Awasthi et al. |
| 8,827,447 B2 | 9/2014 | Awasthi et al. |
| 9,039,174 B2 | 5/2015 | Awasthi et al. |
| 2008/0148689 A1 | 6/2008 | Xia et al. |
| 2009/0173044 A1* | 7/2009 | Linhardt ............... C11D 1/82 53/111 R |

(Continued)

FOREIGN PATENT DOCUMENTS

| | | |
|---|---|---|
| CN | 104321356 A | 1/2015 |
| JP | 2017151437 A | 8/2017 |

(Continued)

OTHER PUBLICATIONS

Lai, Yu-Chin, "The Role of Bulky Polysiloxanylalkyl Methacryates in Polyurethane-Polysiloxane Hydrogels," Journal of Applied Polymer Science, 1996, pp. 1193-1199, vol. 60.

A.T. Bell, "Chemical Reaction in Nonequilibrium Plasmas", Proc. Intl. Conf. Phenom, Ioniz. Gases, 1977, pp. 19-33.

(Continued)

*Primary Examiner* — Charles I Boyer
(74) *Attorney, Agent, or Firm* — Ryan, Mason & Lewis, LLP

(57) ABSTRACT

A packaging system for the storage of an ophthalmic device is disclosed. The packaging system comprises a sealed container containing one or more unused ophthalmic devices immersed in an aqueous packaging solution comprising one or more hydrophilic polymers or copolymers comprising hydrophilic units and endcapped with a hydrophobic end group and a hydrophilic end group, wherein the solution has an osmolality of at least about 200 mOsm/kg, a pH of about 6 to about 9 and is heat sterilized.

28 Claims, No Drawings

(56) References Cited

U.S. PATENT DOCUMENTS

| | | | |
|---|---|---|---|
| 2010/0162661 A1* | 7/2010 | Vanderbilt | C08F 290/046 53/425 |
| 2018/0044518 A1* | 2/2018 | Scales | C08F 290/068 |
| 2018/0113237 A1* | 4/2018 | Chang | C08F 290/142 |
| 2021/0130644 A1* | 5/2021 | Chang | C09D 179/02 |

FOREIGN PATENT DOCUMENTS

| | | |
|---|---|---|
| WO | 9406485 A1 | 3/1994 |
| WO | 9631792 A1 | 10/1996 |
| WO | 2020005416 A1 | 5/2019 |
| WO | 2009089206 A2 | 7/2019 |

OTHER PUBLICATIONS

J. M. Tibbitt et al., "A Model for the Kinetics of Plasma Polymerization", Macromolecules, 1977, 3, pp. 648-653.

M. Tibbitt et al., "Structural Characterization of Plasma-Polymerized Hydrocarbons", J. Macromol. Sci.-Chem., 1976, A10, pp. 1623-1648.

C. P. Ho, et al., "Ultrathin coating of plasma polymer of methane applied on the surface of silicone contact lenses", Mater. Res., 1988, 22, 919-937.

H. Kobayashi et al., "Plasma Polymerization of Saturated and Unsaturated Hydrocarbons", Macromolecules, 1974, 3, pp. 277-283.

H. Yasuda et al., "Polymerization of Organic Compounds in an Electroless Glow Discharge. VI. Acetylene with Unusual Co-monomers", J. of Appl. Poly. Sci., 1975, 19, pp. 2845-2858.

* cited by examiner

CONTACT LENS PACKAGING SOLUTIONS CONTAINING HYDROPHILIC POLYMERS ENDCAPPED WITH A HYDROPHILIC AND A HYDROPHOBIC GROUP

BACKGROUND

The present invention generally relates to packaging solutions for ophthalmic devices such as contact lenses.

Biomedical devices such as ophthalmic lenses made from, for example, silicone-containing materials, have been investigated for a number of years. Such materials can generally be subdivided into two major classes, namely, hydrogels and non-hydrogels. Hydrogels can absorb and retain water in an equilibrium state, whereas non-hydrogels do not absorb appreciable amounts of water. Regardless of their water content, both hydrogel and non-hydrogel silicone medical devices tend to have relatively hydrophobic, non-wettable surfaces that have a high affinity for lipids. This problem is of particular concern with contact lenses.

Those skilled in the art have long recognized the need for modifying the surface of such silicone contact lenses so that they are compatible with the eye. It is known that increased hydrophilicity of the lens surface improves the wettability of the contact lens. This, in turn, is associated with improved wear comfort of contact lenses. Additionally, the surface of the lens can affect the lens's susceptibility to deposition, particularly the deposition of proteins and lipids resulting from tear fluid during lens wear. Accumulated deposition can cause eye discomfort or even inflammation. In the case of extended wear lenses (i.e., lenses used without daily removal of the lens before sleep), the surface is especially important, since extended wear lenses must be designed for high standards of comfort and biocompatibility over an extended period of time.

One approach to enhance wettability of the lens is to carry out a surface post treatment step of the lens. However, the additional step(s) required added cost and time to the manufacturing process.

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking.

It has been stated that if a lens is thoroughly cleaned before insertion, lacrimal fluid can adequately wet the lens. Furthermore, the difficulties of adding a surfactant to a packaging solution, including the possibility of lowering shelf-life and/or adverse reactions during heat sterilization, have further limited the use of surfactants in a packaging solution for the purpose of providing any possible or marginal effect on lens comfort. It is only after a lens has been worn, when proteins or other deposits have formed on the surface of the lens, that surfactants have been used in standard lens-care solutions.

It is highly desirable that contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Accordingly, it would be desirable to provide an improved packaging system for ophthalmic devices such as a contact lens such that the lens would be comfortable to wear in actual use and allow for extended wear of the lens without irritation or other adverse effects to the cornea.

SUMMARY

In accordance with one illustrative embodiment, a packaging system for the storage of an ophthalmic device is provided comprising a sealed container containing one or more unused ophthalmic devices immersed in an aqueous packaging solution comprising one or more hydrophilic polymers or copolymers comprising hydrophilic units and endcapped with a hydrophobic end group and a hydrophilic end group, wherein the solution has an osmolality of at least about 200 mOsm/kg, a pH of about 6 to about 9 and is heat sterilized.

In accordance with a second illustrative embodiment, a method of preparing a packaging system comprising a storable, sterile ophthalmic device is provided, the method comprising: (a) providing an ophthalmic device; (b) immersing the ophthalmic device in an aqueous packaging solution comprising one or more hydrophilic polymers or copolymers comprising hydrophilic units and endcapped with a hydrophobic end group and a hydrophilic end group, wherein the solution has an osmolality of at least about 200 mOsm/kg and a pH in the range of about 6 to about 9; (c) packaging the solution and the ophthalmic device in a manner preventing contamination of the device by microorganisms; and (d) sterilizing the packaged solution and ophthalmic device.

The aqueous packaging solutions for the packaging system of the present invention contain one or more hydrophilic polymers or copolymers comprising hydrophilic units and endcapped with a hydrophobic end group and a hydrophilic end group are believed to provide a more uniform coating on the surface of an ophthalmic device thereby resulting in improved lubricity and/or wettability of the lens. Thus, the lens will be more comfortable to wear in actual use and allow for extended wear of the lens without irritation or other adverse effects to the cornea. Hydrophilic and/or lubricious surfaces of the ophthalmic devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer.

DETAILED DESCRIPTION

The present disclosure provides a packaging system for the storage of ophthalmic devices intended for direct contact with body tissue or body fluid. As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic devices can be any material known in the art capable of forming an ophthalmic device as described above. In one embodiment, an ophthalmic device includes devices which are formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl(meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, an ophthalmic device includes a device which is formed from material hydrophilic per se, since reactive groups, e.g., carboxy, carbamoyl, sulfate, sulfonate, phosphate, amine, ammonium or hydroxy groups, are inherently present in the material and therefore also at the surface of an ophthalmic device manufactured therefrom. Such devices are formed from materials known in the art and include, by way of example, polyhydroxyethyl acrylate, polyhydroxyethyl methacrylate (HEMA), polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon, Atlafilcon and the like. Examples of other suitable bulk materials include balafilcon A, hilafilcon A, alphafilcon A, bilafilcon B and the like.

In another embodiment, an ophthalmic device includes a device which is formed from materials which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed from a bulky silicone monomer (e.g., tris(trimethylsiloxy)silylpropyl methacrylate, commonly known as "TRIS" monomer), methacrylate end-capped poly (dimethylsiloxane)prepolymer, or silicones having fluoroalkyl side groups (polysiloxanes are also commonly known as silicone polymers).

Hydrogels in general are a well-known class of materials that comprise hydrated, crosslinked polymeric systems containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer can function as a crosslinking agent (a crosslinker being defined as a monomer having multiple polymerizable functionalities) or a separate crosslinker may be employed. Silicone hydrogels typically have a water content between about 10 to about 80 weight percent.

Representative examples of useful hydrophilic monomers include, but are not limited to, amides such as N,N-dimethylacrylamide and N,N-dimethylmethacrylamide; cyclic lactams such as N-vinyl-2-pyrrolidone; and (meth)acrylated poly(alkene glycols), such as poly(diethylene glycols) of varying chain length containing monomethacrylate or dimethacrylate end caps. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art. For example, 2-hydroxyethylmethacrylate (HEMA) is a well-known hydrophilic monomer that may be used in admixture with the aforementioned hydrophilic monomers.

The monomer mixtures may also include a second device-forming monomer including a copolymerizable group and a reactive functional group. The copolyermizable group is preferably an ethylenically unsaturated group, such that this device-forming monomer copolymerizes with the hydrophilic device-forming monomer and any other device-forming monomers in the initial device-forming monomer mixture. Additionally, the second monomer can include a reactive functional group that reacts with a complementary reactive group of the copolymer which is the reaction product of one or more polymerizable polyhydric alcohols and one or more polymerizable fluorine-containing monomers. In other words, after the device is formed by copolymerizing the device-forming monomer mixture, the reactive functional groups provided by the second device-forming monomers remain to react with a complementary reactive moiety of the copolymer.

In one embodiment, reactive groups of the second device-forming monomers include epoxide groups. Accordingly, second device-forming monomers are those that include both an ethylenically unsaturated group (that permits the monomer to copolymerize with the hydrophilic device-forming monomer) and the epoxide group (that does not react with the hydrophilic device-forming monomer but remains to react with the copolymer is the reaction product of one or more polymerizable polyhydric alcohols and one or more polymerizable fluorine-containing monomers). Examples include glycidyl methacrylate, glycidyl acrylate, glycidyl vinylcarbonate, glycidyl vinylcarbamate, 4-vinyl-1-cyclohexene-1,2-epoxide and the like.

As mentioned, one class of ophthalmic device substrate materials are silicone hydrogels. In this case, the initial device-forming monomer mixture further comprises a silicone-containing monomer. Applicable silicone-containing monomeric materials for use in the formation of silicone hydrogels are well known in the art and numerous examples are provided in U.S. Pat. Nos. 4,136,250; 4,153,641; 4,740, 533; 5,034,461; 5,070,215; 5,260,000; 5,310,779; and 5,358,995. Specific examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

Representative examples of applicable silicon containing silicone-containing monomers include bulky polysiloxanylalkyl(meth)acrylic monomers. An example of a bulky polysiloxanylalkyl(meth)acrylic monomer is represented by the structure of Formula I:

wherein X denotes —O— or —NR— wherein R denotes hydrogen or a $C_1$ to $C_4$ alkyl; each R independently denotes hydrogen or methyl; each $R^2$ independently denotes a lower alkyl radical, phenyl radical or a group represented by wherein each $R^2$ independently denotes a lower alkyl or phenyl radical; and h is 1 to 10.

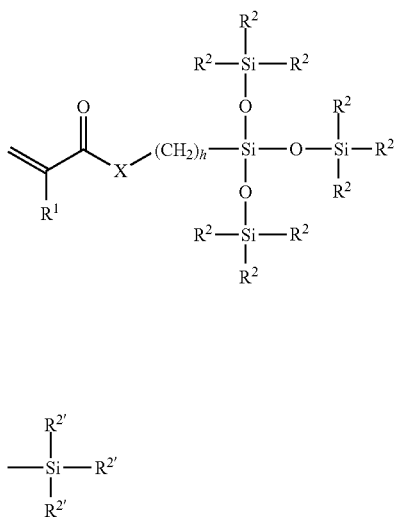

Examples of bulky monomers are methacryloxypropyl tris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, for example, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris (trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

E(*D*A*D*G)$_a$*D*A*D*E'; or (II)

E(*D*G*D*A)$_a$*D*A*D*E'; or (III) wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula IV:

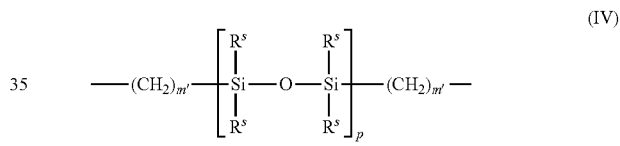

wherein each $R^S$ independently denotes an alkyl or fluoro-substituted alkyl group having 1 to about 10 carbon atoms which may contain ether linkages between the carbon atoms;

m' is at least 1; and p is a number that provides a moiety weight of about 400 to about 10,000;

each of E and E' independently denotes a polymerizable unsaturated organic radical represented by Formula V:

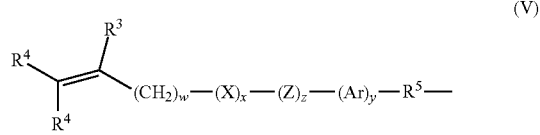

wherein: $R^3$ is hydrogen or methyl;

$R^4$ is hydrogen, an alkyl radical having 1 to 6 carbon atoms, or a —CO—Y—$R^6$ radical wherein Y is —O—, or —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

Ar denotes an aromatic radical having 6 to about 30 carbon atoms;

w is 0 to 6; x is 0 or 1; y is 0 or 1; and z is 0 or 1.

In one embodiment, a silicone-containing urethane monomer is represented by Formula VI:

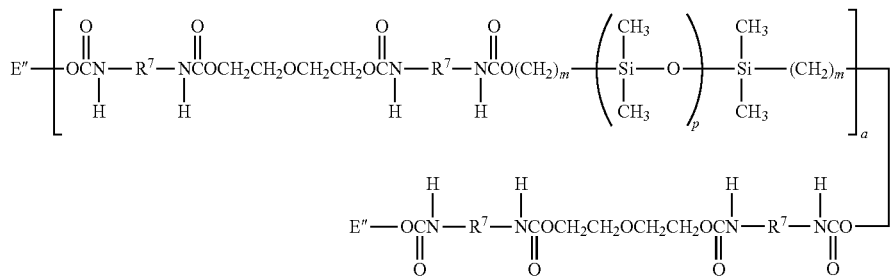

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

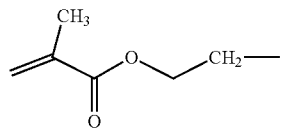

In another embodiment, a silicone hydrogel material comprises (in bulk, that is, in the monomer mixture that is copolymerized) about 5 to about 50 percent, or from about 10 to about 25, by weight of one or more silicone macromonomers, about 5 to about 75 percent, or about 30 to about 60 percent, by weight of one or more polysiloxanyl-alkyl (meth)acrylic monomers, and about 10 to about 50 percent, or about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. The silane macromonomer may be a silicon-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that have been disclosed in various publications and are being continuously developed for use in contact lenses and other medical devices can also be used. For example, a biomedical device can be formed from at least a cationic monomer such as cationic silicone-containing monomer or cationic fluorinated silicone-containing monomers.

Contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product is of particular importance for silicone hydrogels, primarily due to the inclusion of silicone-containing monomers which may tend to separate from the hydrophilic comonomer.

Suitable organic diluents include, for example, monohydric alcohols such as $C_6$ to $C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure.

Generally, the diluent may be included at about 5 to about 60 percent by weight of the monomeric mixture. In one embodiment, the diluent may be included at about 10 to about 50 percent by weight of the monomeric mixture. If necessary, the cured lens may be subjected to solvent removal, which can be accomplished by evaporation at or near ambient pressure or under vacuum. An elevated temperature can be employed to shorten the time necessary to evaporate the diluent.

Following removal of the organic diluent, the lens can then be subjected to mold release and optional machining operations. The machining step includes, for example, buffing or polishing a lens edge and/or surface. Generally, such machining processes may be performed before or after the article is released from a mold part. As an example, the lens may be dry released from the mold by employing vacuum tweezers to lift the lens from the mold.

As one skilled in the art will readily appreciate, ophthalmic device surface functional groups of the ophthalmic device may be inherently present at the surface of the device. However, if the ophthalmic device contains too few or no functional groups, the surface of the device can be modified by known techniques, for example, plasma chemical methods (see, for example, WO 94/06485), or conventional functionalization with groups such as —OH, —$NH_2$ or —$CO_2H$. Suitable ophthalmic device surface functional groups of the biomedical device include a wide variety of groups well known to the skilled artisan. Representative examples of such functional groups include, but are not limited to, hydroxy groups, amino groups, carboxy groups, carbonyl groups, aldehyde groups, sulfonic acid groups, sulfonyl chloride groups, isocyanato groups, carboxy anhydride groups, lactone groups, azlactone groups, epoxy groups and groups being replaceable by amino or hydroxy groups, such as halo groups, or mixtures thereof. In one embodiment, the ophthalmic device surface functional groups of the ophthalmic device are amino groups and/or hydroxy groups.

In one embodiment, the foregoing ophthalmic devices are subjected to an oxidative surface treatment such as corona discharge or plasma oxidation followed by treatment with the aqueous packaging solution according to the present invention. For example, an ophthalmic device such as a silicone hydrogel formulation containing hydrophilic polymers, such as poly(N,N-dimethylacrylamide) or poly(N-vinylpyrrolidinone), is subjected to an oxidative surface treatment to form at least silicates on the surface of the lens and then the lens is treated with an aqueous packaging solution according to the present invention to render a lubricious, stable, highly wettable surface coating. The complexation treatment is advantageously performed under autoclave conditions (sterilization conditions).

The standard process such as a plasma process (also referred to as "electrical glow discharge processes") provides a thin, durable surface upon the ophthalmic device prior to binding the brush copolymer to at least a portion of the surface thereof. Examples of such plasma processes are provided in U.S. Pat. Nos. 4,143,949; 4,312,575; and 5,464,667.

Although plasma processes are generally well known in the art, a brief overview is provided below. Plasma surface treatments involve passing an electrical discharge through a gas at low pressure. The electrical discharge may be at radio frequency (typically 13.56 MHz), although microwave and other frequencies can be used. Electrical discharges produce ultraviolet (UV) radiation, in addition to being absorbed by atoms and molecules in their gas state, resulting in energetic electrons and ions, atoms (ground and excited states), molecules, and radicals. Thus, a plasma is a complex mixture of atoms and molecules in both ground and excited states, which reach a steady state after the discharge is begun. The circulating electrical field causes these excited atoms and molecules to collide with one another as well as the walls of the chamber and the surface of the material being treated.

The deposition of a coating from a plasma onto the surface of a material has been shown to be possible from high-energy plasmas without the assistance of sputtering (sputter-assisted deposition). Monomers can be deposited from the gas phase and polymerized in a low pressure atmosphere (about 0.005 to about 5 torr, and preferably about 0.001 to about 1 torr) onto a substrate utilizing continuous or pulsed plasmas, suitably as high as about 1000 watts. A modulated plasma, for example, may be applied about 100 milliseconds on then off. In addition, liquid nitrogen cooling has been utilized to condense vapors out of the gas phase onto a substrate and subsequently use the plasma to chemically react these materials with the substrate. However, plasmas do not require the use of external cooling or heating to cause the deposition. Low or high wattage (e.g., about 5 to about 1000, and preferably about 20 to about 500 watts) plasmas can coat even the most chemical-resistant substrates, including silicones.

After initiation by a low energy discharge, collisions between energetic free electrons present in the plasma cause the formation of ions, excited molecules, and free-radicals. Such species, once formed, can react with themselves in the gas phase as well as with further ground-state molecules. The plasma treatment may be understood as an energy dependent process involving energetic gas molecules. For chemical reactions to take place at the surface of the lens, one needs the required species (element or molecule) in terms of charge state and particle energy. Radio frequency plasmas generally produce a distribution of energetic species. Typically, the "particle energy" refers to the average of the so-called Boltzman-style distribution of energy for the energetic species. In a low-density plasma, the electron energy distribution can be related by the ratio of the electric field strength sustaining the plasma to the discharge pressure (E/p). The plasma power density P is a function of the wattage, pressure, flow rates of gases, etc., as will be appreciated by the skilled artisan. Background information on plasma technology, hereby incorporated by reference, includes the following: A. T. Bell, Proc. Intl. Conf. Phenom. Ioniz. Gases, "Chemical Reaction in Nonequilibrium Plasmas", 19-33 (1977); J. M. Tibbitt, R. Jensen, A. T. Bell, M. Shen, Macromolecules, "A Model for the Kinetics of Plasma Polymerization", 3, 648-653 (1977); J. M. Tibbitt, M. Shen, A. T. Bell, J. Macromol. Sci.-Chem., "Structural Characterization of Plasma-Polymerized Hydrocarbons", A10, 1623-1648 (1976); C. P. Ho, H. Yasuda, J. Biomed, Mater. Res., "Ultrathin coating of plasma polymer of methane applied on the surface of silicone contact lenses", 22, 919-937 (1988); H. Kobayashi, A. T. Bell, M. Shen, Macromolecules, "Plasma Polymerization of Saturated and Unsaturated Hydrocarbons", 3, 277-283 (1974); R. Y. Chen, U.S. Pat. No. 4,143,949, Mar. 13, 1979, "Process for Putting a Hydrophilic Coating on a Hydrophobic Contact Lens"; and H. Yasuda, H. C. Marsh, M. O. Bumgarner, N. Morosoff, J. of Appl. Poly. Sci., "Polymerization of Organic Compounds in an Electroless Glow Discharge. VI. Acetylene with Unusual Co-monomers", 19, 2845-2858 (1975).

Based on this previous work in the field of plasma technology, the effects of changing pressure and discharge power on the rate of plasma modification can be understood. The rate generally decreases as the pressure is increased. Thus, as pressure increases the value of E/p, the ratio of the electric field strength sustaining the plasma to the gas pressure decreases and causes a decrease in the average electron energy. The decrease in electron energy in turn causes a reduction in the rate coefficient of all electron-molecule collision processes. A further consequence of an increase in pressure is a decrease in electron density. Providing that the pressure is held constant, there should be a linear relationship between electron density and power.

In practice, contact lenses are surface-treated by placing them, in their unhydrated state, within an electric glow discharge reaction vessel (e.g., a vacuum chamber). Such reaction vessels are commercially available. The lenses may be supported within the vessel on an aluminum tray (which acts as an electrode) or with other support devices designed to adjust the position of the lenses. The use of a specialized support devices which permit the surface treatment of both sides of a lens are known in the art and may be used herein.

As mentioned above, the surface of the lens, for example, a silicone hydrogel continuous-wear lens is initially treated, e.g., oxidized, by the use of a plasma to render the subsequent brush copolymer surface deposition more adherent to the lens. Such a plasma treatment of the lens may be accomplished in an atmosphere composed of a suitable media, e.g., an oxidizing media such as oxygen, air, water, peroxide, $O_2$ (oxygen gas), etc., or appropriate combinations thereof, typically at an electric discharge frequency of about 13.56 Mhz, or between about 20 to about 500 watts at a pressure of about 0.1 to about 1.0 torr, or for about 10 seconds to about 10 minutes or more, or about 1 to about 10 minutes. It is preferred that a relatively "strong" plasma is utilized in this step, for example, ambient air drawn through a five percent (5%) hydrogen peroxide solution. Those skilled in the art will know other methods of improving or promoting adhesion for bonding of the subsequent brush copolymer layer.

Next, the ophthalmic device such as a lens will be immersed in an aqueous packaging solution and stored in a packaging system according to the present invention. Generally, a packaging system for the storage of an ophthalmic device according to the present invention includes at least a sealed container containing one or more unused ophthalmic devices immersed in an aqueous packaging solution. In one embodiment, the sealed container is a hermetically sealed blister-pack, in which a concave well containing an ophthalmic device such as a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

The aqueous packaging solution will contain one or more hydrophilic polymers or copolymers comprising hydrophilic units and endcapped with a hydrophobic end group and a hydrophilic end group, wherein the solution has an osmolality of at least about 200 mOsm/kg, a pH of about 6 to about 9 and is heat sterilized. The term "hydrophilic" as used herein shall be understood to mean a polymer or copolymer containing polar or charged functional groups rendering it water-soluble. In general, the one or more hydrophilic polymers or copolymers comprising hydrophilic units and endcapped with a hydrophobic end group and a hydrophilic end group are prepared via RAFT polymerization, i.e., monomers are polymerized via a RAFT mechanism to form the polymer or copolymers, e.g., a block or random copolymer in which the molecular weight of each of the units and the entire polymer can be precisely controlled. Thus, RAFT polymerization is a radical polymerization technique that enables polymers to be prepared having a well-defined molecular architecture and low polydispersity.

RAFT agents suitable for use in the RAFT polymerization to obtain the one or more hydrophilic polymers or copolymers are based upon thio carbonyl thio chemistry which is well known to those of ordinary skill in the art. The RAFT agent can be, for example, a xanthate-containing compound, trithiocarbonate-containing compound, dithiocarbamate-containing compound or dithio ester-containing compound, wherein each compound contains a thiocarbonyl thio group. One class of RAFT agents that can be used herein is of the general formula:

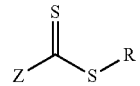

wherein Z is a substituted oxygen (e.g., xanthates (—O—R)), a substituted nitrogen (e.g., dithiocarbamates (—NRR)), a substituted sulfur (e.g., trithiocarbonates (—S—R)), a substituted or unsubstituted aryl group (e.g., phenyl, and naphthyl), a substituted or unsubstituted $C_1$-$C_{20}$ alkyl or $C_3$-$C_{25}$ unsaturated, or partially or fully saturated ring (e.g., dithioesters (—R)) or a carboxylic acid-containing group; and R is independently a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a $C_1$-$C_{20}$ ester group; an ether or polyether-containing group; an alkyl- or arylamide group; an alkyl- or arylamine group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; and combinations thereof.

Representative examples of alkyl groups for use herein include, by way of example, a straight or branched alkyl chain radical containing carbon and hydrogen atoms of from 1 to about 30 carbon atoms and preferably from 1 to about 12 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms and preferably from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4, 4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms and preferably from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms and preferably from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronaphthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of ester groups for use herein include, by way of example, a carboxylic acid ester having one to 30 carbon atoms or from 6 to 28 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxides) such as ethylene oxide, propylene oxide, butylene oxide, poly(ethylene oxides), poly(ethylene glycols), poly(propylene oxides), poly(butylene oxides) and mixtures or copolymers thereof, an ether or polyether group of the general formula —$(R^2OR^3)_t$, wherein $R^2$ is a bond, a substituted or unsubstituted alkyl, cycloalkyl or aryl group as defined herein and $R^3$ is a substituted or unsubstituted alkyl, cycloalkyl or aryl group as defined herein and t is at least 1, e.g., —$CH_2CH_2OC_6H_5$ and $CH_2$—$CH_2$—$CH_2$—O—$CH_2$—$(CF_2)_z$—H where z is 1 to 6, —$CH_2CH_2OC_2H_5$, and the like.

Representative examples of alkyl or arylamide groups for use herein include, by way of example, an amide of the general formula —$R^4C(O)NR^5R^6$ wherein $R^4$, $R^5$ and $R^6$ are independently $C_1$-$C_{30}$ hydrocarbons, e.g., $R^4$ can be alkylene groups, arylene groups, cycloalkylene groups and $R^5$ and $R^6$ can be alkyl groups, aryl groups, and cycloalkyl groups as defined herein and the like.

Representative examples of alkyl or arylamine groups for use herein include, by way of example, an amine of the general formula —$R^7N$ $R^8R^9$ wherein $R^7$ is a $C_2$-$C_{30}$ alkylene, arylene, or cycloalkylene and $R^8$ and $R^9$ are independently $C_1$-$C_{30}$ hydrocarbons such as, for example, alkyl groups, aryl groups, or cycloalkyl groups as defined herein.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized, and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroquinolinyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, iso-oxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocylic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined herein directly bonded to an alkyl group as defined herein. The heterocycloalkyl radical may be attached to the main structure at any carbon atom in the alkyl group that results in the creation of a stable structure.

The substituents in the 'substituted oxygen', 'substituted nitrogen', 'substituted sulfur', 'substituted alkyl', 'substituted alkylene, 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring' may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, and the like.

Representative examples of a carboxylic acid-containing group for use herein include, by way of example, a carboxylic acid group attached to the rest of the molecule via a linking group, e.g., of the general formula —R$^{11}$C(O)OH, wherein R$^{11}$ is a bond, a substituted or unsubstituted alkylene group, a substituted or unsubstituted cycloalkylene group, a substituted or unsubstituted cycloalkylalkylene group, a substituted or unsubstituted arylene or a substituted or unsubstituted arylalkylene group as defined herein, e.g., —CH(Ar)(C(O)OH), —C(CH$_3$)(C(O)OH), and the like, wherein the carboxylic acid group can be attached to the substituent or attached directly to alkylene group, cycloalkylene group, cycloalkylalkylene group, arylene or arylalkylene group.

Representative examples of RAFT agents for use herein include, but are not limited to, dodecyl-2-((ethyoxycarbonothioyl)thio)propanoate, octadecyl-2-((ethyoxycarbonothioyl)thio)propanoate, dodecyl-2-(dodecyl trithiocarbonyl) propanoate, octadecyl-2-(dodecyl trithiocarbonyl) propanoate, PDMS-containing systems such as ethoxypropyl poly(dimethylsiloxane)-α-(o-ethyl xanthyl)propanoate, and ethoxypropyl poly(dimethylsiloxane)-α-(dodecyl trithiocarbonyl) propanoate) and the like and mixtures thereof. As one skilled in the art will readily appreciate, although the above exemplified RAFT agents were prepared using readily available dodecyl and octadecyl alcohols, it is contemplated that any other fatty alcohol (e.g., a fatty alcohol containing from 10 carbon atoms to 20 carbon atoms.

There is no particular limitation on the organic chemistry used to form the RAFT agent and is within the purview of one skilled in the art. Also, the working examples below provide guidance. For example, the RAFT agents can be prepared as exemplified in Schemes I-IV below.

SCHEME I

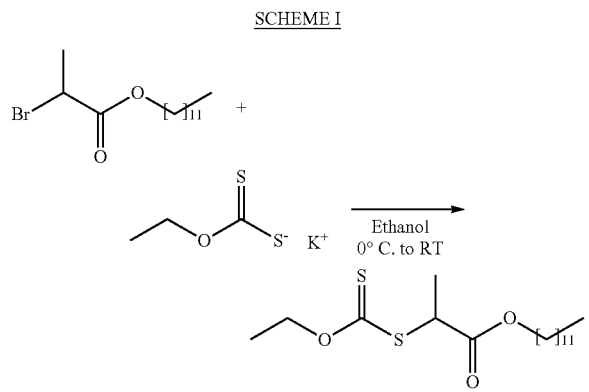

SCHEME II

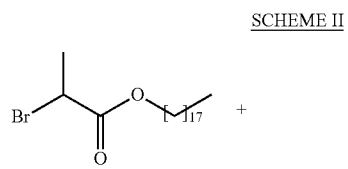

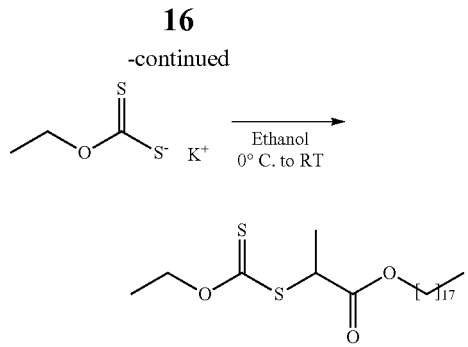

SCHEME III

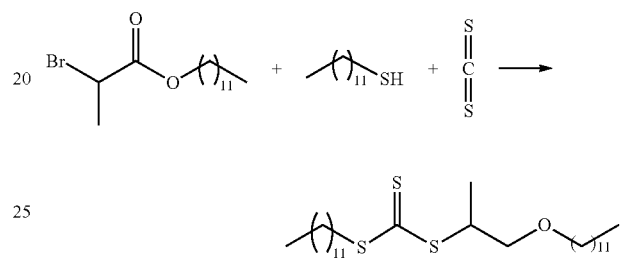

SCHEME IV

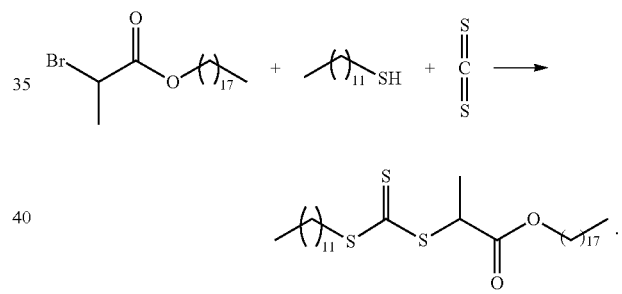

Suitable hydrophobic end groups include, for example, a straight or branched C$_3$ to C$_{18}$ alkyl group, a C$_3$ to C$_{30}$ cycloalkyl group, a C$_6$ to C$_{30}$ aryl group, a C$_7$ to C$_{30}$ arylalkyl group, a fluorine substituted straight or branched C$_3$ to C$_{18}$ alkyl group, a fluorine substituted C$_3$ to C$_{30}$ cycloalkyl group, a fluorine substituted C$_6$ to C$_{30}$ aryl group, a fluorine substituted C$_7$ to C$_{30}$ arylalkyl group, a polydimethylsiloxane, an organosilicon-containing monomer and the like. In one embodiment, a polydimethylsiloxane can include, for example, from 2 to about 50 dimethyl siloxanyl repeating units. For example, a RAFT agent containing a hydrophobic polydimethylsiloxane end group can be represented by the following structures:

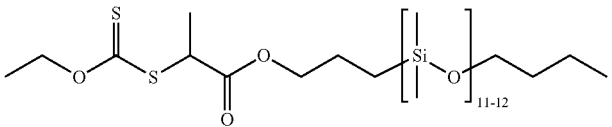

-continued

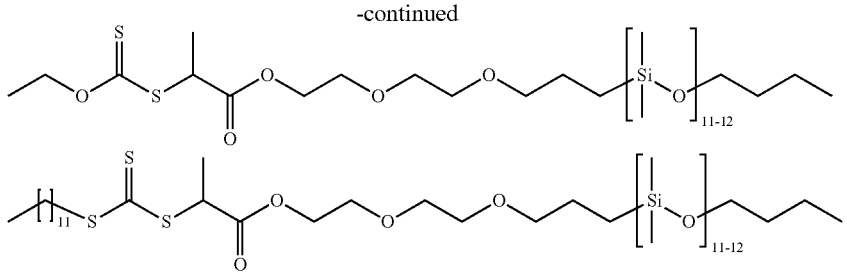

An "organosilicon-containing monomer" as used herein contains at least one [siloxanyl] or at least one [silyl-alkyl-siloxanyl] repeating unit, in a monomer, macromer or prepolymer. In one embodiment, the total Si and attached O are present in the organosilicon-containing monomer in an amount greater than about 5 weight percent, or greater than about 30 weight percent of the total molecular weight of the organosilicon-containing monomer. Organosilicon-containing hydrophobic monomers are known in the art, see, e.g., U.S. Pat. Nos. 4,195,030, 4,208,506, 4,327,203, 4,355,147, 7,915,323, 7,994,356, 8,420,711, 8,827,447 and 9,039,174, the contents of which are incorporated by reference herein.

In one embodiment, an organosilicon-containing monomer can comprise a compound represented by a structure of Formula I:

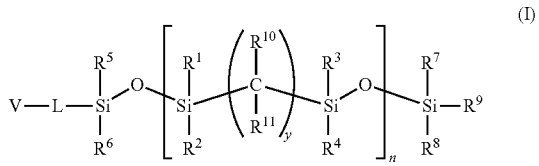

wherein V is ethylenically unsaturated polymerizable group, L is a linker group or a bond; $R^1$, $R^2$, $R^3$, $R^4$, $R^5$, $R^6$, $R^7$, $R^8$, and $R^9$ are independently H, $C_1$ to $C_{12}$ alkyl, halo alkyl, $C_3$ to $C_{12}$ cycloalkyl, heterocycloalkyl, $C_2$ to $C_{12}$ alkenyl, haloalkenyl, or $C_6$ to $C_{12}$ aromatic; $R^{10}$, and $R^{11}$ are independently H or $C_1$ to $C_{12}$ alkyl wherein at least one of $R^{10}$ and $R^{11}$ is hydrogen; y is 2 to 7 and n is 1 to 100 or from 1 to 20.

Ethylenically unsaturated polymerizable groups are well known to those skilled in the art. Suitable ethylenically unsaturated polymerizable groups include, for example, (meth)acrylates, vinyl carbonates, O-vinyl carbamates, N-vinyl carbamates, and (meth)acrylamides. As used herein, the term "(meth)" denotes an optional methyl substituent. Thus, terms such as "(meth)acrylate" denotes either methacrylate or acrylate, and "(meth)acrylamide" denotes either methacrylamide or acrylamide.

Linker groups can be any divalent radical or moiety and include, for example, substituted or unsubstituted $C_1$ to $C_{12}$ alkyl, alkyl ether, alkenyls, alkenyl ethers, halo alkyls, substituted or unsubstituted siloxanes, and monomers capable of propagating ring opening.

In one embodiment, V is a (meth)acrylate, L is a $C_1$ to $C_{12}$ alkylene, $R^1$, $R^2$, $R^3$, $R^4$, $R^5$, $R^6$, $R^7$, $R^8$, and $R^9$ are independently a $C_1$ to $C_{12}$ alkyl, $R^{10}$ and $R^{11}$ are independently H, y is 2 to 7 and n is 3 to 8.

In one embodiment, V is a (meth)acrylate, L is a $C_1$ to $C_6$ alkyl, $R^1$, $R^2$, $R^3$, $R^4$, $R^5$, $R^6$, $R^7$, $R^8$, and $R^9$ are independently a $C_1$ to $C_6$ alkyl, $R^{10}$ and $R^{11}$ are independently H, y is 2 to 7 and n is 1 to 20.

In one embodiment, an organosilicon-containing monomers can comprise a compound represented by a structure of Formula II:

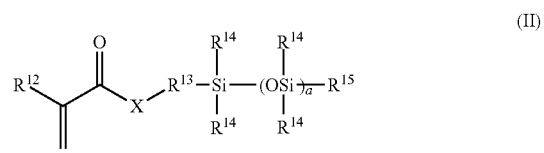

wherein $R^{12}$ is H or methyl; X is O or $NR^{16}$; wherein $R^{16}$ is selected from H, or $C_1$ to $C_4$ alkyl, which may be further substituted with one or more hydroxyl groups, and in some embodiments is H or methyl; $R^{13}$ is a divalent alkyl group, which may further be functionalized with a group selected from the group consisting of ether groups, hydroxyl groups, carbamate groups and combinations thereof, and in another embodiment $C_1$ to $C_6$ alkylene groups which may be substituted with ether, hydroxyl and combinations thereof, and in yet another embodiment $C_1$ or $C_3$ to $C_4$ alkylene groups which may be substituted with ether, hydroxyl and combinations thereof; each $R^{14}$ is independently a phenyl or $C_1$ to $C_4$ alkyl which may be substituted with fluorine, hydroxyl or ether, and in another embodiment each $R^{14}$ is independently selected from ethyl and methyl groups, and in yet another embodiment, each $R^{14}$ is methyl; $R^{15}$ is a $C_1$ to $C_4$ alkyl; a is 2 to 50, and in some embodiments 5 to 15.

As discussed below, the hydrophilic end group can be the end hydrophilic unit of the hydrophilic units in the hydrophilic polymer or copolymer or can be derived from a hydrophilic group different from the end hydrophilic unit of the hydrophilic units introduced into the hydrophilic polymer or copolymer.

The RAFT polymerization is then carried out by forming hydrophilic units in the RAFT agent. The number of hydrophilic units in the hydrophilic polymer or copolymer can vary widely, e.g., the number of hydrophilic units can range from about 10 to about 3000. In one embodiment, the number of hydrophilic units in the hydrophilic polymer or copolymer can range from about 50 to about 100. In general, the hydrophilic units are derived from at least one ethylenically unsaturated polymerizable hydrophilic monomer. The term "ethylenically unsaturated polymerizable" as used herein shall be understood to include, by way of example, (meth)acrylate-containing radicals, (meth)acrylamide-containing radicals, vinyl-containing radicals such as vinyl radicals, vinyl carbonate-containing radicals, vinyl carbamate-containing radicals and the like, styrene-containing radicals, itaconate-containing radicals, vinyloxy-containing radicals, fumarate-containing radicals, maleimide-containing radicals, vinyl sulfonyl radicals and the like. In one embodiment, the at least one ethylenically unsaturated polymerizable hydrophilic monomer is selected from the group consisting of an acrylamide, an acetamide, a formamide, a cyclic lactam, a (meth)acrylated alcohol, a (meth)acrylated poly(alkyleneoxy), an ethylenically unsaturated carboxylic acid, a vinyl carbonate, vinyl carbamate, oxazolone monomer, and mixtures thereof.

Suitable ethylenically unsaturated polymerizable hydrophilic monomers include, by way of example, acrylamides such as N,N-dimethylacrylamide, N,N-dimethylmethacrylamide, and the like; acetamides such as N-vinyl-N-methyl acetamide, N-vinyl acetamide and the like; formamides such as N-vinyl-N-methyl formamide, N-vinyl formamide, and the like; cyclic lactams such as N-vinyl-2-pyrrolidone and the like; (meth)acrylated alcohols such as 2-hydroxyethyl methacrylate, 2-hydroxyethyl acrylate and the like; (meth) acrylated poly(ethyleneglycol)s and the like; ethylenically unsaturated carboxylic acids such as methacrylic acid, acrylic acid and the like; N-vinylcarbamates of low molecular weight alcohols (i.e., an alcohol having from 1 to 6 carbon atoms) such as N-vinyl methyl carbamate, N-vinyl ethyl carbamate, N-vinyl n-propylcarbamate, N-vinyl iso-propylcarbamate, and the like; acrylamides and mixtures thereof.

In one embodiment, the RAFT polymerization can be carried out by forming hydrophilic units derived from an ethylenically unsaturated polymerizable monomer having ring-opening reactive functionalities in the RAFT agent. Such monomers may include, for example, one or more ring-opening reactive groups such as azlactone, epoxy, acid anhydrides, and the like. Suitable polymerizable monomers having ring-opening reactive functionalities include, but are not limited to, glycidyl methacrylate (GMA), maleic anhydride, itaconic anhydride and the like and mixtures thereof. The units derived from an ethylenically unsaturated polymerizable monomer having ring-opening reactive functionalities can be copolymerized with a hydrophilic comonomer to form hydrophilic units in the resulting random copolymer. Non-limiting examples of comonomers useful to be copolymerized with the ring-opening reactive functionalities of the monomer to form random copolymers used to prepare a biomedical device include those mentioned above, with dimethylacrylamide, hydroxyethyl methacrylate (HEMA), and/or N-vinylpyrrolidone being preferred.

In another embodiment, the RAFT polymerization can be carried out by forming hydrophilic units derived from an ethylenically unsaturated polymerizable alkoxylated polymer in the RAFT agent. Suitable ethylenically unsaturated polymerizable alkoxylated polymers include, by way of example, polymerizable polyethylene glycols having a molecular weight of up to, for example, about 1000 such as those with CTFA names PEG-200, PEG-400, PEG-600, PEG-1000, and mixtures thereof. Representative examples include PEG-200 methacrylate, PEG-400 methacrylate, PEG-600 methacrylate, PEG-1000 methacrylate and the like and mixtures thereof.

There is no particular limitation on the organic chemistry used to form the RAFT agent with hydrophilic units and is within the purview of one skilled in the art. Also, the working examples below provide guidance. For example, the RAFT agent with hydrophilic units can be obtained by (1) mixing the hydrophilic monomer and RAFT agent; (2) adding a polymerization initiator; (3) and subjecting the monomer/initiator mixture to a source of heat. Typical initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobis-isobutyronitrile (AIBN). The level of initiator employed will vary within the range of 0.01 to 2 weight percent of the mixture of monomers. If desired, the mixture of the above-mentioned monomers is warmed with addition of a free-radical former.

The reaction can be carried out at a temperature of between about 40° C. to about 120° C. for a time period of about 30 minutes to about 48 hours. If desired, the reaction can be carried out in the presence of a suitable solvent. Suitable solvents are in principle all solvents which dissolve the monomer used, for example, 1,4-dioxane, hexanol, dimethylformamide; acetone, cyclohexanone, toluene, t-butyl methyl ether, tetrahydrofuran, and the like and mixtures thereof.

In general, the RAFT agents with hydrophilic units can be prepared as exemplified in Schemes I-IV below.

SCHEME I

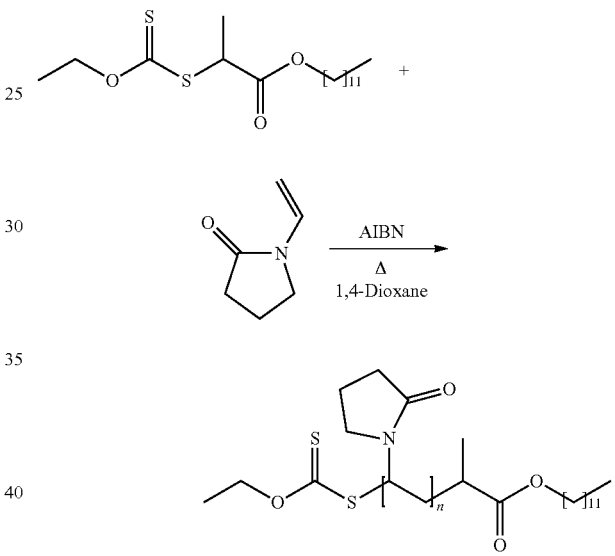

SCHEME II

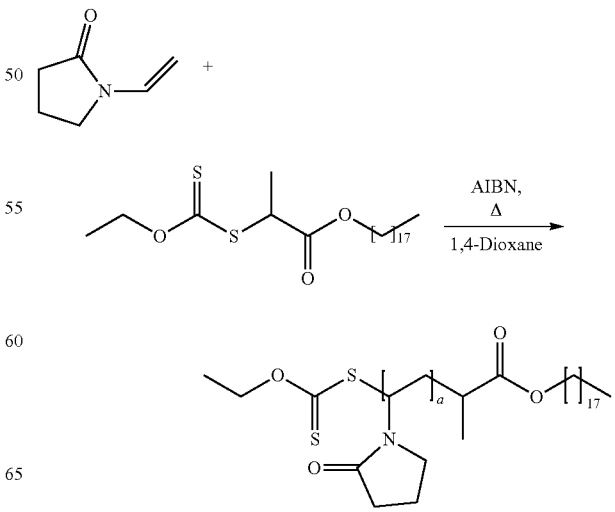

SCHEME III

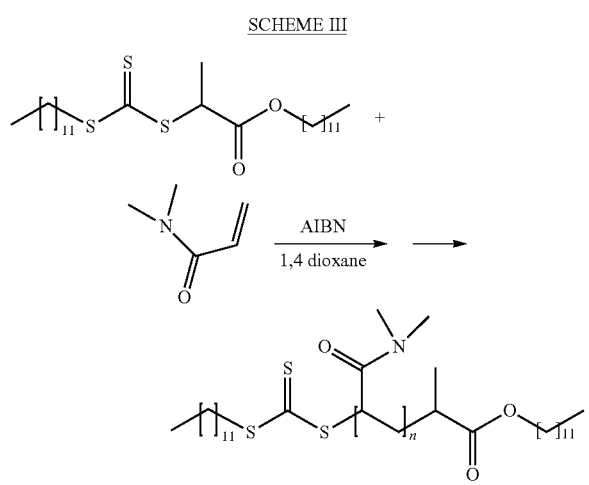

SCHEME IV

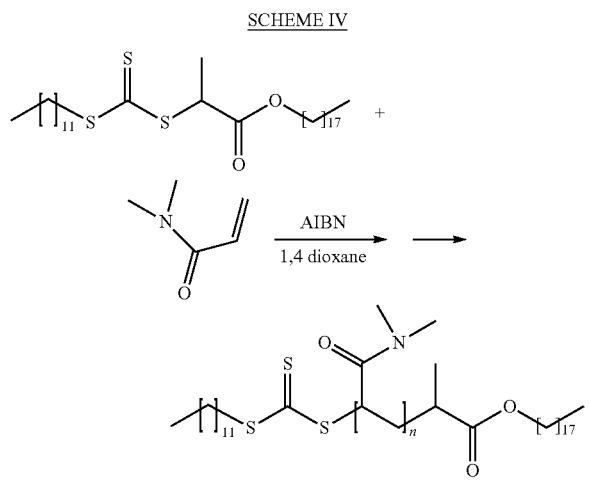

Next, the RAFT group of the RAFT agent, i.e., the thio carbonyl thio group, is removed to obtain the resulting hydrophilic polymer or copolymer comprising hydrophilic units and end-capped with a hydrophobic end group and a hydrophilic end group by methods known in the art. For example, the replacement of the RAFT terminal functionality is carried out by first reacting the RAFT agent with a free radical initiator (e.g., AIBN), and then endcapping the hydrophilic polymer or copolymer with either hydrophilic group, e.g., by recombination of the initiator fragment (e.g., to obtain a —CN group or a solvent-derived radical, i.e. —OH group) or a terminal hydrogen atom, e.g., hydrogen atom abstraction from solvent to generate the terminal —H group.

The resulting hydrophilic polymer or copolymer comprising hydrophilic units and endcapped with a hydrophobic end group and a hydrophilic end group can have a number average molecular weight ranging from about 1500 to about 75,000 Da. In one embodiment, the resulting hydrophilic polymer or copolymer comprising hydrophilic units and endcapped with a hydrophobic end group and a hydrophilic end group can have a number average molecular weight ranging from about 4000 to about 20,000 Da.

The amount of the hydrophilic polymer or copolymer comprising hydrophilic units and endcapped with a hydrophobic end group and a hydrophilic end group employed in a packaging solution for storing an ophthalmic device in a packaging system of the present invention is an amount effective to improve the surface properties of the ophthalmic device. It is believed these polymers enhance initial and extended comfort when a contact lens, packaged in the solution and then removed from the packaging system, is placed on the eye for wearing. In one embodiment, the concentration of a hydrophilic polymer or copolymer comprising hydrophilic units and endcapped with a hydrophobic end group and a hydrophilic end group present in the packaging solution will range from about 0.01% to about 10% w/w. In one embodiment, the concentration of a hydrophilic polymer or copolymer comprising hydrophilic units and endcapped with a hydrophobic end group and a hydrophilic end group present in the packaging solution will range from about 0.1% to about 5% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. In one embodiment, the liquid media is aqueous-based. A particularly useful aqueous liquid medium is that derived from saline, for example, a conventional saline solution or a conventional buffered saline solution.

The pH of the packaging solutions should be maintained within the range of about 6 to about 9, or from about 6.5 to about 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and $KH_2PO_4$) and mixtures thereof. Generally, buffers will be used in amounts ranging from about 0.05 to about 2.5 percent by weight of the solution. In one embodiment, buffers will be used in amounts ranging from about 0.1 to about 1.5 percent by weight of the solution. The packaging solutions of this invention preferably contain a borate buffer, containing one or more of boric acid, sodium borate, potassium tetraborate, potassium metaborate or mixtures of the same.

Typically, the packaging solutions are also adjusted with tonicity agents, to approximate the osmotic pressure of normal lacrimal fluids which is equivalent to a 0.9 percent solution of sodium chloride or 2.5 percent of glycerol solution. The packaging solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Suitable tonicity adjusting agents include, for example, sodium and potassium chloride, dextrose, glycerin, calcium and magnesium chloride and the like and mixtures thereof. These tonicity adjusting agents are typically used individually in amounts ranging from about 0.01 to about 2.5% w/v. In one embodiment, the tonicity adjusting agents are used in amounts ranging from about 0.2 to about 1.5% w/v. The tonicity agent will be employed in an amount to provide a final osmotic value of at least about 200 mOsm/kg. In one embodiment, the tonicity adjusting agents are used in an amount to provide a final osmotic value of from about 200 to about 400 mOsm/kg. In one embodiment, the tonicity adjusting agents are used in an amount to provide a final osmotic value of from about 250 to about 350 mOsm/kg. In one embodiment, the tonicity adjusting agents are used in an amount to provide a final osmotic value of from about 280 to about 320 mOsm/kg.

If desired, one or more additional components can be included in the packaging solution. Such additional component or components are chosen to impart or provide at least one beneficial or desired property to the packaging solution. In general, the additional components may be selected from components which are conventionally used in one or more ophthalmic device care compositions. Suitable additional components include, for example, cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Suitable sequestering agents include, for example, disodium ethylene diamine tetraacetate, alkali metal hexametaphosphate, citric acid, sodium citrate and the like and mixtures thereof.

Suitable viscosity builders include, for example, hydroxyethyl cellulose, hydroxymethyl cellulose, polyvinyl pyrrolidone, polyvinyl alcohol and the like and mixtures thereof.

Suitable antioxidants include, for example, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to the present invention includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the packaging solution may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the present invention.

In one embodiment, the steps leading to the present ophthalmic device packaging system includes (1) molding an ophthalmic device in a mold comprising at least a first and second mold portion, (2) hydrating and cleaning the device in a container comprising at least one of the mold portions, (3) introducing the packaging solution with the copolymer into the container with the device supported therein, and (4) sealing the container. In one embodiment, the method also includes the step of sterilizing the contents of the container. Sterilization may take place prior to, or most conveniently after, sealing of the container and may be effected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims. In the examples, the following abbreviations are used.

NVP: N-vinyl-2-pyrrolidone
DMA: N,N-dimethylacetamide
AIBN: azo bis-isobutylnitrile
DI: Deionized water Example 1

Preparation of PDMA-C12 having the following structure:

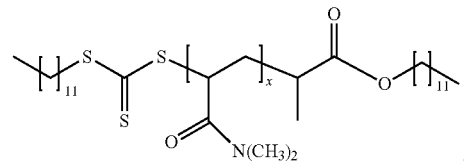

Step 1—Synthesis of Dodecyl-2-bromopropanoate

To a 1000 mL round bottom 3-neck flask equipped with magnetic stirrer, condenser, addition funnel and temperature probe was dissolved 1-dodecanol (18.63 g) in 300 mL of ethyl ether. Next, the addition funnel was charged with triethylamine (15.33 mL) dissolved in 10 mL of ethyl ether and added mixture dropwise to reaction flask. When addition was finished, the addition funnel was washed with 90 mL of ethyl ether. The reaction flask was placed in an ice/water bath, and charged addition funnel with 2-bromopropionyl bromide (11.11 mL) dissolved in 50 mL of ethyl ether. Once the internal temperature reached 0° C., dropwise addition of 2-bromopropionyl bromide/ethyl ether solution was carried out over a 2 hour period. The addition funnel was washed with remaining ethyl ether, stirred reaction and allowed to reach room temperature overnight. The next day the reaction mixture was worked up 3 times with 150 mL of 10% (v:v) HCL solution, 3 times with 150 mL of deionized water, and 1 time 150 mL 5% (w:v) NaCl solution. The organic layer was collected and dried over magnesium sulfate for 1 hour, filtered and solvent was removed under reduced pressure. The crude material was then column cleaned using a silica gel column as the stationary phase and 95:5 (v: v) heptane: ethyl acetate as mobile phase.

Step 2—Synthesis of Dodecyl-2-(dodecyl trithiocarbonyl) propanoate

In a 2-necked 250-mL round bottom flask equipped with magnetic stir bar, condenser, and addition funnel was stirred carbon disulfide (7.279 g) and dodecanethiol (9.675 g) in 33 mL of chloroform under $N_2$ blanket. To the addition funnel was added triethylamine (9.674 g) dissolved in 5 mL of chloroform dropwise to reaction flask. The reaction mixture was stirred for 3 hours at room temperature. After three hours added dropwise via addition funnel dodecyl-2-bromopropanoate (15.37 g) of step 1 with 32 mL chloroform. The reaction mixture was stirred for 24 hours, then washed with 2×160 mL DI water, 2×160 mL 5% HCl, and 2×160 mL 5% NaCl. The organic layers were collected and dried over magnesium sulfate and filtered. The solvent was removed under pressure and the resulting product further purified via column chromatography over silica gel using 95:5 heptane/ethyl acetate.

Step 3-Polymerization of N,N-dimethylacetamide using Dodecyl-2-(dodecyltrithiocarbonyl)propionate A 250 mL round bottom 3-neck flask equipped with magnetic stirrer, condenser, nitrogen inlet was charged with DMA (40 g), 1,4-dioxane (100 mL), and dodecyl-2-(dodecyltrithiocarbonyl)propionate of Example 2 (0.244 g). The reaction mixture was purged under nitrogen for 1 hour. After purging the reaction mixture, AIBN (0.736 mg) was added to the reaction flask and dropped reaction flask into a pre-heated 60° C. oil bath. The polymerization was allowed to run for 26 hours. After 26 hours allowed reaction flask to cool down to room temperature and precipitated reaction mixture into 2600 mL of ethyl ether. The polymer was filtered and collected, and the collected polymer was dried under reduced pressure overnight. The resulting Polymer was crushed and stored in an amber glass bottle stored in a dry box. GPC Results of polymer (RI-GPC): Mn=62,500 Da, Mw=93,200 Da and PD=1.49 Yield=87.5%.

Step 4-Removal of RAFT Group

To a 500 mL round bottom 2-neck flask equipped with magnetic stirrer, condenser, and nitrogen inlet was added the polymer of step 3 (70 g) and isopropyl alcohol (280 mL). The reaction mixture was purged under nitrogen for 1 hour. After purging the reaction mixture, AIBN (4.52 g) was added to the reaction flask and dropped reaction flask into a pre-heated 60° C. oil bath. The reaction was allowed to run for 20 hours. After 20 hours, the reaction flask was allowed to cool down to room temperature and precipitated reaction mixture into 2600 mL of ethyl ether. The polymer was filtered and collected, and the collected polymer was dried under reduced pressure overnight. The resulting polymer was crushed and stored in an amber glass bottle stored in a dry box.

Example 2

Preparation of PDMA-18 having the following structure:

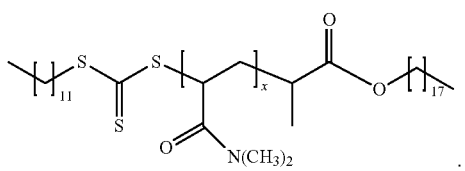

Step 1-Synthesis of Octadecyl-2-bromopropanoate

To a 1000 mL round bottom 3-neck flask equipped with magnetic stirrer, condenser, addition funnel and temperature probe was dissolved 1-octadecanol (27.05 g) in 300 mL of ethyl ether. Next, the addition funnel was charged with triethylamine (15.33 mL) dissolved in 10 mL of ethyl ether and added mixture dropwise to reaction flask. When the addition was finished, the addition funnel was washed with 90 mL of ethyl ether. The reaction flask was placed in an ice/water bath, charged addition funnel with 2-bromopropionyl bromide (11.11 mL) dissolved in 50 mL of ethyl ether. Once the internal temperature reached 0° C., dropwise addition of 2-bromopropionyl bromide/ethyl ether solution was carried out over a 2 hour period. The addition funnel was washed with remaining ethyl ether, stirred reaction and allowed to reach room temperature overnight. The next day the reaction mixture was worked up 3 times with 150 mL of 10% (v:v) HCL solution, 3 times with 150 mL of deionized water, and 1 time 150 mL 5% (w:v)NaCl solution. The organic layer was collected and dried over magnesium sulfate for 1 hour, filtered and the solvent was removed under reduced pressure. The crude material was then column cleaned using a silica gel column as the stationary phase and 95:5 (v: v) heptane:ethyl acetate as mobile phase.

Step 2-Synthesis of octadecyl-2-(dodecyltrithiocarbonyl)propionate

In a 2-necked 250-mL round bottom flask equipped with magnetic stir bar, condenser, and addition funnel was stirred carbon disulfide (4.09 g) and dodecanethiol (5.437 g) in 33 mL of chloroform under N$_2$ blanket. To the addition funnel was added triethylamine (5.436 g) dissolved in 5 mL of chloroform dropwise to the reaction flask. The reaction mixture was stirred for 3 hours at room temperature. After three hours, added dropwise via addition funnel octadecyl-2-bromopropanoate (12.o g) of step 1 with 32 mL chloroform. The reaction mixture was stirred for 24 hours, then washed with 2×160 mL DI water, 2×160 mL 5% HCl, and 2×160 mL 5% NaCl. The organic layers were collected and dried over magnesium sulfate and filtered. The solvent removed under pressure.

Step 3-Polymerization of N,N-dimethylacetamide using octadecyl-2-(dodecyltrithiocarbonyl)propionate To a 250 mL round bottom 3-neck flask equipped with magnetic stirrer, condenser, nitrogen inlet, was charged with DMA (40 g), 1,4-dioxane (100 mL), and octadecyl-2-(dodecyltrithiocabonyl)propionate (0.546 g) of step 2. The reaction mixture was purged under nitrogen for 1 hour. After purging the reaction mixture, AIBN (1.48 mg) was added to the reaction flask and dropped reaction flask into a pre-heated 60° C. oil bath. The polymerization was allowed to run for 26 hours. After 26 hours, the reaction flask was allowed to cool down to room temperature and precipitated reaction mixture into 2600 mL of ethyl ether. The resulting polymer was filtered and collected, and then dried under reduced pressure overnight. The polymer was crushed and stored in an amber glass bottle stored in a dry box. GPC Results of polymer (RI-GPC): Mn=40,900 Da; Mw=50,600 Da and PD=1.24 Yield=100%.

Step 4-Removal of RAFT Group

To a 500 mL round bottom 2-neck flask equipped with magnetic stirrer, condenser, and nitrogen inlet was added the polymer of step 3 (70 g) and isopropyl alcohol (280 mL). The reaction mixture was purged under nitrogen for 1 hour.

After purging the reaction mixture, AIBN (4.52 g) was added to the reaction flask and dropped reaction flask into a pre-heated 60° C. oil bath. The reaction was allowed to run for 20 hours. After 20 hours, the reaction flask was allowed to cool down to room temperature and precipitated reaction mixture into 2600 mL of ethyl ether. The polymer was filtered and collected, and the collected polymer was dried under reduced pressure overnight. The resulting polymer was crushed and stored in an amber glass bottle stored in a dry box.

Example 3

Preparation of PVP-C12 having the following structure:

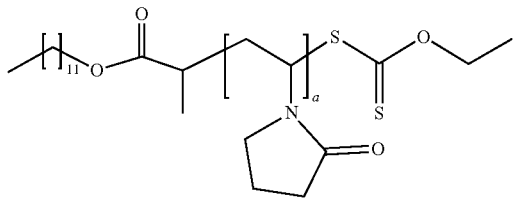

Step 1-Synthesis of Dodecyl-2-bromopropanoate

To a 1000 mL round bottom 3-neck flask equipped with magnetic stirrer, condenser, addition funnel and temperature probe was dissolved 1-dodecanol (18.63 g) in 300 mL of ethyl ether. Next, the addition funnel was charged with triethylamine (15.33 mL) dissolved in 10 mL of ethyl ether and added mixture dropwise to reaction flask. When addition was finished, the addition funnel was washed with 90 mL of ethyl ether. The reaction flask was placed in an ice/water bath, and charged addition funnel with 2-bromopropionyl bromide (11.11 mL) dissolved in 50 mL of ethyl ether. Once the internal temperature reached 0° C., dropwise addition of 2-bromopropionyl bromide/ethyl ether solution was carried out over a 2 hour period. The addition funnel was washed with remaining ethyl ether, stirred reaction and allowed to reach room temperature overnight. The next day the reaction mixture was worked up 3 times with 150 mL of 10% (v:v) HCL solution, 3 times with 150 mL of deionized water, and 1 time 150 mL 5% (w:v) NaCl solution. The organic layer was collected and dried over magnesium sulfate for 1 hour, filtered and solvent was removed under reduced pressure. The crude material was then column cleaned using a silica gel column as the stationary phase and 95:5 (v: v) heptane: ethyl acetate as mobile phase.

Step 2—Synthesis of Dodecyl-2-((ethyoxycarbonothioyl)thio)propanoate

To a 250 mL round bottom 3-neck flask equipped with magnetic stirrer, condenser, nitrogen blanket and temperature probe was dissolved dodecyl-2-bromopropanoate (6.350 g) of step 1 in 70 mL of ethyl ether, and purged under nitrogen for 30 minutes. The reaction flask was placed in an ice/water bath, and once internal temperature reached 0° C. potassium ethyl xanthate (3.484 g) was added using a powder funnel. The powder funnel was washed with 7 mL of ethanol, and the reaction mixture was stirred and allowed to reach room temperature overnight. The next day the reaction mixture was extracted 4 times with 50 mL 2:1 Heptane:Ethyl ether. The organic layers were collected, dried over magnesium sulfate for 1 hour, and filtered. The solvent was removed under reduced pressure. The crude material was then column cleaned using a silica gel column as the stationary phase and 99:1 (v: v) Heptane:Ethyl acetate as mobile phase.

Step 3—Polymerization of N-Vinyl Pyrrolidone Using dodecyl-2-((ethyoxycarbonothioyl)thio)propanoate To a 250 mL round bottom 3-neck flask equipped with magnetic stirrer, condenser, nitrogen inlet, was charged with NVP (40 g), 1,4-dioxane (40 mL), and dodecyl-2-((ethoxycarbonothioyl)thio)propanoate (1.954 g) of step 2. The reaction mixture was purged under nitrogen for 1 hour. After purging mixture, AIBN (8.85 mg) was added to the reaction flask. The reaction flask was dropped into a pre-heated 60° C. oil bath, and polymerization was allowed to run for 26 hours. After 26 hours, the reaction flask was allowed to cool down to room temperature and the reaction mixture was precipitated into 2600 mL of ethyl ether. The resulting polymer was filtered, collected and dried under reduced pressure overnight. The polymer was crushed and stored in an amber glass bottle stored in a dry box. GPC Results of polymer (RI-GPC): Mn=6,700 Da, Mw=7,100 Da and PD=1.06 Yield=84%.

Step 4—Removal of RAFT Group

To a 500 mL round bottom 2-neck flask equipped with magnetic stirrer, condenser, and nitrogen inlet was added the polymer of step 3 (70 g) and isopropyl alcohol (280 mL). The reaction mixture was purged under nitrogen for 1 hour. After purging the reaction mixture, AIBN (4.52 g) was added to the reaction flask and dropped reaction flask into a pre-heated 60° C. oil bath. The reaction was allowed to run for 20 hours. After 20 hours, the reaction flask was allowed to cool down to room temperature and precipitated reaction mixture into 2600 mL of ethyl ether. The polymer was filtered and collected, and the collected polymer was dried under reduced pressure overnight. The resulting polymer was crushed and stored in an amber glass bottle stored in a dry box.

Example 4

Preparation of PVP-C18 having the following structure:

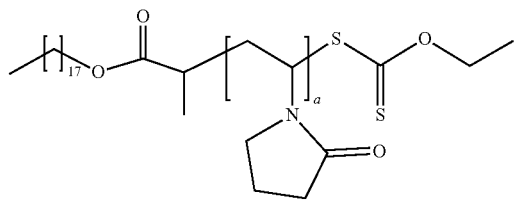

Step 1—Synthesis of Octadecyl-2-bromopropanoate

To a 1000 mL round bottom 3-neck flask equipped with magnetic stirrer, condenser, addition funnel and temperature probe was dissolved 1-octadecanol (27.05 g) in 300 mL of ethyl ether. Next, the addition funnel was charged with triethylamine (15.33 mL) dissolved in 10 mL of ethyl ether and added mixture dropwise to reaction flask. When the addition was finished, the addition funnel was washed with 90 mL of ethyl ether. The reaction flask was placed in an ice/water bath, charged addition funnel with 2-bromopropionyl bromide (11.11 mL) dissolved in 50 mL of ethyl ether. Once the internal temperature reached 0° C., dropwise addition of 2-bromopropionyl bromide/ethyl ether solution was carried out over a 2 hour period. The addition funnel was washed with remaining ethyl ether, stirred reaction and allowed to reach room temperature overnight. The next day the reaction mixture was worked up 3 times with 150 mL of 10% (v:v) HCL solution, 3 times with 150 mL of deionized water, and 1 time 150 mL 5% (w:v)NaCl solution. The organic layer was collected and dried over magnesium sulfate for 1 hour, filtered and the solvent was removed under reduced pressure. The crude material was then column cleaned using a silica gel column as the stationary phase and 95:5 (v: v) heptane:ethyl acetate as mobile phase.

Step 2—Synthesis of octadecyl-2-((ethyoxycarbonothioyl)thio)propanoate

To a 250 mL round bottom 3-neck flask equipped with magnetic stirrer, condenser, nitrogen blanket and temperature probe was dissolved octadecyl-2-bromopropanoate (6.350) of step 1 in 70 mL of ethyl ether, and purged under nitrogen for 30 minutes. The reaction flask was placed in an ice/water bath, and once internal temperature reached 0° C. potassium ethyl xanthate (3.484 g) was added using a powder funnel. The powder funnel was washed with 7 mL of ethanol, and the reaction mixture was stirred and allowed to reach room temperature overnight. The next day the reaction mixture was extracted 4 times with 50 mL 2:1 heptane:ethyl ether. The organic layers were collected, dried over magnesium sulfate for 1 hour and filtered. The solvent was removed under reduced pressure. The crude material was then column cleaned using a silica gel column as the stationary phase and 99:1 (v: v) heptane:ethyl acetate as mobile phase.

Step 3—Polymerization of N-Vinyl Pyrrolidone Using octadecyl-2-((ethyoxycarbonothioyl)thio)propanoate To a 250 mL round bottom 3-neck flask equipped with magnetic stirrer, condenser, nitrogen inlet was charged with NVP (40 g), 1,4-dioxane (40 mL), and octadecyl-2-((ethoxycarbonothioyl)thio)propanoate (0.301 g) of step 2. The reaction mixture was purged under nitrogen for 1 hour. After purging the reaction mixture, AIBN (11.1 mg) was added to the reaction flask and dropped into a pre-heated 60° C. oil bath. The polymerization was allowed to run for 26 hours. After 26 hours, the reaction flask was allowed to cool down to room temperature and the reaction mixture was precipitated into 2600 mL of ethyl ether. The resulting polymer was filtered, collected and dried under reduced pressure overnight. The polymer was crushed and stored in an amber glass bottle stored in a dry box. GPC Results of polymer (RI-GPC): Mn=31,300 Da; Mw=41,300 Da and PD=1.32 Yield=74%.

Step 4—Removal of RAFT Group

To a 500 mL round bottom 2-neck flask equipped with magnetic stirrer, condenser, and nitrogen inlet was added the polymer of step 3 (70 g) and isopropyl alcohol (280 mL). The reaction mixture was purged under nitrogen for 1 hour. After purging the reaction mixture, AIBN (4.52 g) was added to the reaction flask and dropped reaction flask into a pre-heated 60° C. oil bath. The reaction was allowed to run for 20 hours. After 20 hours, the reaction flask was allowed to cool down to room temperature and precipitated reaction mixture into 2600 mL of ethyl ether. The polymer was filtered and collected, and the collected polymer was dried under reduced pressure overnight. The resulting polymer was crushed and stored in an amber glass bottle stored in a dry box.

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A packaging system for the storage of an ophthalmic device comprising a sealed container containing one or more unused ophthalmic devices immersed in an aqueous packaging solution comprising one or more hydrophilic polymers or copolymers comprising hydrophilic units, the one or more hydrophilic polymers or copolymers having a hydrophobic terminal end group and a hydrophilic terminal end group, wherein the aqueous packaging solution has an osmolality of at least about 200 mOsm/kg, a pH of about 6 to about 9 and is heat sterilized.

2. The packaging system of claim 1, wherein the ophthalmic device is a contact lens.

3. The packaging system of claim 1, wherein the hydrophilic units are derived from at least one ethylenically unsaturated polymerizable hydrophilic monomer.

4. The packaging system of claim 3, wherein the at least one ethylenically unsaturated polymerizable hydrophilic monomer is selected from the group consisting of an acrylamide, an acetamide, a formamide, a cyclic lactam, a (meth)acrylated alcohol, a (meth)acrylated poly(alkyleneoxy), an ethylenically unsaturated carboxylic acid, a hydrophilic vinyl carbonate, a hydrophilic vinyl carbamate, a hydrophilic oxazolone monomer, and mixtures thereof.

5. The packaging system of claim 1, wherein the hydrophilic terminal end group of the one or more hydrophilic polymers or copolymers is —OH or —CN.

6. The packaging system of claim 1, wherein the hydrophilic terminal end group of the one or more hydrophilic polymers or copolymers is an end hydrophilic unit of the hydrophilic units.

7. The packaging system of claim 1, wherein the hydrophilic units comprise from about 10 to about 3000 units.

8. The packaging system of claim 1, wherein the one or more hydrophilic polymers or copolymers are derived from reversible addition fragmentation chain transfer (RAFT) polymerization.

9. The packaging system of claim 1, wherein the hydrophobic terminal end group is selected from the group consisting of a straight or branched $C_3$ to $C_{18}$ alkyl group, a $C_3$ to $C_{30}$ cycloalkyl group, a $C_6$ to $C_{30}$ aryl group, a $C_7$ to $C_{30}$ arylalkyl group, a fluorine substituted straight or branched $C_3$ to $C_{18}$ alkyl group, a fluorine substituted $C_3$ to $C_{30}$ cycloalkyl group, a fluorine substituted $C_6$ to $C_{30}$ aryl groups, a fluorine substituted $C_7$ to $C_{30}$ arylalkyl group, a polydimethylsiloxane and an organosilicon-containing monomer.

10. The packaging system of claim 1, wherein the one or more hydrophilic polymers or copolymers have a number average molecular weight ranging from about 1,500 Da to about 75,000 Da.

11. The packaging system of claim 1, wherein a concentration of the one or more hydrophilic polymers or copolymers in the aqueous packaging solution ranges from about 0.01% to about 10% w/w.

12. The packaging system of claim 1, wherein a concentration of the one or more hydrophilic polymers or copolymers in the aqueous packaging solution ranges from about 0.1 to about 5% w/w.

13. The packaging system of claim 1, wherein the aqueous packaging solution further comprises a buffer agent, a tonicity adjusting agent, a cleaning agent, a wetting agent, a nutrient agent, a sequestering agent, a viscosity builder, a contact lens conditioning agent, an antioxidant, and mixtures thereof.

14. The packaging system of claim 1, wherein the sealed container is heat sterilized subsequent to sealing of the container and the aqueous packaging solution does not contain an effective disinfecting amount of a disinfecting agent or a germicide compound.

15. The packaging system of claim 1, wherein the aqueous packaging solution does not contain an effective disinfecting amount of a disinfecting agent.

16. The packaging system of claim 1, wherein the aqueous packaging solution does not contain a germicide compound.

17. A method of preparing a packaging system comprising a storable, sterile ophthalmic device, the method comprising:
(a) providing an ophthalmic device;
(b) immersing the ophthalmic device in an aqueous packaging solution comprising one or more hydrophilic polymers or copolymers comprising hydrophilic units, the one or more hydrophilic polymers or copolymers having a hydrophobic terminal end group and a hydrophilic terminal end group, wherein the aqueous packaging solution has an osmolality of at least about 200 mOsm/kg and a pH in the range of about 6 to about 9;
(c) packaging the aqueous packaging solution and the ophthalmic device in a manner preventing contamination of the ophthalmic device by microorganisms; and
(d) sterilizing the packaged solution and the ophthalmic device.

18. The method of claim 17, wherein the ophthalmic device is a contact lens.

19. The method of claim 17, wherein the hydrophilic units are derived from at least one ethylenically unsaturated polymerizable hydrophilic monomer selected from the group consisting of an acrylamide, an acetamide, a formamide, a cyclic lactam, a (meth)acrylated alcohol, a (meth)acrylated poly(alkyleneoxy), an ethylenically unsaturated carboxylic acid, a hydrophilic vinyl carbonate, a hydrophilic vinyl carbamate, a hydrophilic oxazolone monomer, and mixtures thereof.

20. The method of claim 17, wherein the hydrophilic terminal end group of the one or more hydrophilic polymers or copolymers is —OH and —CN.

21. The method of claim 17, wherein the hydrophilic terminal end group of the one or more hydrophilic polymers or copolymers is an end hydrophilic unit of the hydrophilic units.

22. The method of claim 17, wherein the hydrophilic units comprise from about 10 to about 3000 units.

23. The method of claim 17, wherein the one or more hydrophilic polymers or copolymers are derived from reversible addition fragmentation chain transfer (RAFT) polymerization.

24. The method of claim 17, wherein the hydrophobic terminal end group is selected from the group consisting of a straight or branched $C_3$ to $C_{18}$ alkyl group, a $C_3$ to $C_{30}$ cycloalkyl group, a $C_6$ to $C_{30}$ aryl group, a $C_7$ to $C_{30}$ arylalkyl group, a fluorine substituted straight or branched $C_3$ to $C_{18}$ alkyl group, a fluorine substituted $C_3$ to $C_{30}$ cycloalkyl group, a fluorine substituted $C_6$ to $C_{30}$ aryl groups, a fluorine substituted $C_7$ to $C_{30}$ arylalkyl group, a polydimethylsiloxane and an organosilicon-containing monomer.

25. The method of claim 17, wherein the one or more hydrophilic polymers or copolymers have a number average molecular weight ranging from about 1,500 Da to about 75,000 Da.

26. The method of claim 17, wherein a concentration of the one or more hydrophilic polymers or copolymers in the aqueous packaging solution ranges from about 0.01% to about 10% w/w.

27. The method of claim 17, wherein the aqueous packaging solution further comprises a buffer agent, a tonicity adjusting agent, a cleaning agent, a wetting agent, a nutrient agent, a sequestering agent, a viscosity builder, a contact lens conditioning agent, an antioxidant, and mixtures thereof.

28. The method of claim 17, wherein sterilizing the packaged solution and the ophthalmic device comprises heat sterilizing the packaged solution and the ophthalmic device, and the aqueous packaging solution does not contain an effective disinfecting amount of a disinfecting agent or a germicide compound.

* * * * *